United States Patent [19]

Steinman et al.

[11] Patent Number: 4,554,103

[45] Date of Patent: Nov. 19, 1985

[54] PREPARATION OF 4-ACYLOXYAZETIDINONES FROM ACYL NITRATES AND PENAMS

[75] Inventors: Martin Steinman, Livingston; Yee-Shing Wong, Belleville, both of N.J.

[73] Assignee: Schering Corporation, Kenilworth, N.J.

[21] Appl. No.: 513,887

[22] Filed: Jul. 14, 1983

[51] Int. Cl.[4] ............................................ C07D 205/08
[52] U.S. Cl. ............................ 260/239 A; 260/545 R
[58] Field of Search .................................. 260/239 AL

[56] References Cited

U.S. PATENT DOCUMENTS

| 4,260,618 | 4/1981 | Christensen | 424/263 |
| 4,260,627 | 4/1981 | Christensen | 424/274 |
| 4,282,150 | 8/1981 | Nenarel | 260/239 A |
| 4,301,074 | 11/1981 | Christensen et al. | 260/245.2 R |

FOREIGN PATENT DOCUMENTS 0013662  7/1980  European Pat. Off. .
0042026 12/1981  European Pat. Off. .
0082113  6/1983  European Pat. Off. .

OTHER PUBLICATIONS

Louw et al, Chem. Abs. 86, 4884q, (1976).
Morse, et al, Chem. Abs. 86, 4886s, (1976).
Suaroto et al. *Tetrahedron Letters,* No. 42, pp. 4059–4062, (1978).

*Primary Examiner*—Mark L. Berch
*Attorney, Agent, or Firm*—Thomas D. Hoffman; Gerald S. Rosen; Anita W. Magatti

[57] ABSTRACT

There is disclosed a high yielding process for cleaving penicillinates with acyl or aroyl nitrates to produce acyloxy or aroyloxy azetidinones which are intermediates in the multistep process for producing penems from penicillinates.

2 Claims, No Drawings

PREPARATION OF 4-ACYLOXYAZETIDINONES FROM ACYL NITRATES AND PENAMS

BACKGROUND

This invention relates to an improvement in one step of the multistep process of preparing penems from penams. More particularly, this invention relates to an improvement in the process step of cleaving the thiazolidine ring of a 6-substituted penicillanic acid ester and replacing the sulfur with an acyloxy or aroyloxy group, using an acyl nitrate or aroyl nitrate as the ring cleaving agent.

Penems are prepared by a multistep process from 6aminopenicillanic acid (6-APA). Thus, for example, 6-APA is converted to methyl (5R,6S,8R)-6-(1-hydroxyethyl)penicillanate by converting the 6-APA to (5R)-6,6-dibromopenicillanic acid with sodium bromide, esterifying the (5R)-6,6-dibromopenicillanic acid to the methyl ester with dimethylsulfate, introducing the (1-hydroxyethyl) substitutent to the 6-position with ethyl magnesium bromide and acetaldehyde then debrominating with zinc dust and ammonium chloride. The resulting methyl (5R,6S,8R)6-(1-hydroxyethyl)penicillinate can then be converted to a 4-acyloxy or aroyloxy azetidinone by cleaving the thiazolidine ring of the penicillinate.

U.S. Pat. No. 4,301,074 discloses one widely used method in which mercuric acetate is the cleaving agent. This method has the disadvantage of requiring a means to dispose of or recycle the mercury. Suaroto et al, Tetrahedron Letters No. 42, 4059-62 (1978) disclose a method in which the penicillinate is converted to the 1-oxide then cleaved with a carboxylic acid in the presence of trimethylphosphite. This method requires the use of the 1-oxide penam.

The 4-acyloxy or aroyloxy azetidinone which results from the known process is then converted by a series of steps, all of which are known in the art, to the desired penem.

BRIEF DESCRIPTION

This invention provides a process for preparing in high yields a 4-acyloxy or 4-aroyloxy azetidinone represented by the formula

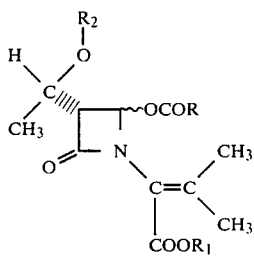

wherein
R is lower alkyl, phenyl or phenyl substituted with up to three substituents independently selected from nitro, halo or lower alkyl;
$R_1$ is lower alkyl, allyl or a metabolizable ester group;
$R_2$ is a readily removable hydroxy protecting group; and
the wavy line means either the R stereochemical configuration, the S stereochemical configuration or a mixture thereof.

DETAILED DESCRIPTION OF THE INVENTION

The process comprises treating a penam with an acyl or aroyl nitrate to yield a nitro substituted azetidinone as illustrated in the following reaction scheme A:

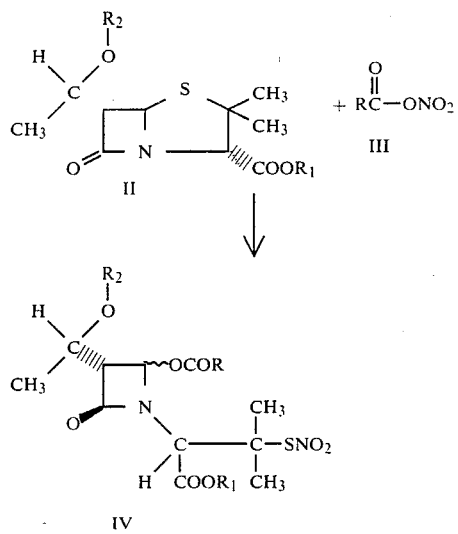

wherein R, $R_1$ and $R_2$ are as defined above.

This reaction is carried out in the cold, e.g. about 5°-20° C. in an inert organic solvent, e.g. a halogenated hydrocarbon such as 1,2-dichloroethane. The reaction takes up to about 12 hours to complete.

The intermediate compound IV is then converted to compound I without the need to isolate it from the reaction mixture. This is accomplished by treating the intermediate in the reaction mixture with triethyl amine according to the following reaction scheme B:

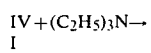

This reaction takes place in the organic phase of reaction A and is completed in about 4 to 8 hours. The resulting product is recovered in high yields, e.g. about 85%, based on the starting penam.

As used herein and throughout the specification, "lower alkyl" means a straight or branched chain alkyl of from 1 to 6 carbons, e.g. methyl, ethyl, propyl, isopropyl, butyl, pentyl and the like; "halo" means a halogen such as chlorine or bromine; "metabolizable ester group" means physiologically cleavable esters, i.e. those esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl. These esters are prepared by conventional procedures for making esters of penicillins.

The term "removable hydroxy protecting group" means any such group conventionally used for this purpose with the only requirement being compatability with the hydroxy substituent on penems and removability utilizing elemental zinc or any other conventional agent for this purpose which will not adversely affect the penem structure. Preferred are those groups which have an oxycarbonyl moiety, e.g. trichloroethoxycarbonyl, paranitrobenzyloxycarbonyl and trimethylsilyloxycarbonyl.

The acyl or aroyl nitrate reactant is prepared by conventional means, i.e. reaction of the corresponding acid anhydride with nitric acid. The preferred nitrate is acetylnitrate.

The following examples illustrate the invention.

EXAMPLE 1

Acetyl Nitrate

Cool 50 ml of 1,2-dichloroethane and 50 ml of acetic anhydride (0.5 mole) at 10° C. under nitrogen using a drying tube. Add 0.5 ml of concentrated sulfuric acid followed by 8 ml of 90% nitric acid (0.2 mole) dropwise to the mixture with stirring at 10°–15° C. for 2.5 hours. The product, acetyl nitrate, is used without isolation in the succeeding reaction with a penicillinate ester as in Example 3 below.

EXAMPLE 2

Propionyl Nitrate

Add to 6.5 ml of propionic anhydride (0.05 mole) in 5 ml of 1,2-dichloroethane under nitrogen using a drying tube, 2 drops of concentrated sulfuric acid and then add 0.8 ml of 90% nitric acid (0.02 mole) dropwise with stirring at 20° C. (inside temperature) for 3 hours. The product, propionyl nitrate, is not isolated in the succeeding reaction with a penicillinate ester as in example 4 below.

Following the procedures of Examples 1 and 2 an aroyl nitrate such as benzoyl nitrate can be prepared using the appropriate acid anhydride.

EXAMPLE 3

(3S,5R)-1-[2-methyl-1-methoxycarbonylprop-1-enyl]-3-(1-trichloroethoxy-carbonyloxyethyl)-4-acetoxyazetidin-2-one Add 43.5 g of methyl (5R,6S,8R)-6-(1-trichloroethoxycarbonyloxyethyl)penicillanate [prepared as described in DiNinno et al, J. Org. Chem. 42, 2960 (1977)] in 50 ml of 1,2-dichloroethane slowly at 10°–15° C. to the final reaction mixture of Example 1. After addition is completed, stir the mixture at 15° C. for 3 hours and pour into 200 ml of ice-water with stirring overnight at room temperature. Separate the organic layer and wash with water (200 ml). Add triethylamine (50 ml) slowly to the cold organic mixture with stirring for 4 hours (pH>10), and then wash with water (3×100 ml). Remove the solvent under vacuum to dryness. Chromatograph the residue on silicagel (hexane/methylene chloride=1:1) to obtain the title compound as an oil in 87% yield based on the starting penicillanate.

EXAMPLE 4

(3S,5R)-1-[2-methyl-1-methoxycarbonylprop-1-enyl]-3-(1-trichloroethoxycarbonyloxyethyl)-4-propionoxyazetidin-2-one Add 4.3 g of methyl(5R,6S,8R)-6-(1-trichloroethoxycarbonyloxyethyl)penicillinate in 5 ml of 1,2-dichloroethane slowly at 15° C. to the final reaction mixture of Example 2. After addition is completed, stir the mixture at 20° C. for 4 hours, and pour into 20 ml of icewater with stirring overnight at room temperature. Separate the organic layer and wash with water (20 ml). Add triethylamine (5 ml) slowly to the cold organic mixture with stirring for 4 hours (pH>10), and then wash with water (3×10 ml). Treat the organic layer with 30 ml of sodium hypochlorite (Clorox). Separate the organic layer, stir with 5 ml triethylamine for 3 hours and then wash with water (3×20 ml). Dry the organic layer over anhydrous sodium sulfate and filter through silica gel. Remove the solvent to dryness to obtain the title compound as an oil in 80% yield based on the starting penicillanate.

The compounds of formula I in which R is phenyl or substituted phenyl can be prepared in high yields by the methods Examples 3 and 4 by utilizing the appropriate nitrate reagent.

The compounds of formula I are intermediates for the preparation of penems having antibacterial activity.

The compounds of formula I are first converted to 3-(1-trichloroethoxycarbonyloxyethyl)-4-acetoxyazetidin-2-one by known means, e.g. by treatment with potassium permanganate, see for instance U.S. Pat. No. 4,301,074. The following example illustrates the preparation of a penem from the latter azetidin-2-one compound.

EXAMPLE 5

(5R,6S,8R)sodium-6-(1-hydroxyethyl)-2-ethylthiopenem-3-carboxylate (a) Add to a 250 ml flask 7.8 g (0.0223 moles) of 3-(1-trichloroethoxycarbonyloxyethyl)-4-acetoxyazetidin2-one, 220 ml acetonitrile, 2.6 gms (0.252 moles) cesium carbonate, and 5.2 gm (0.0188 moles) triphenylmethanethiol (tritylthiol). After stirring for 5 hours, an additional 1.0 gm (0.0036 moles) triphenylmethanethiol is added and the mixture is stirred for another one-half hour. After overnight refrigeration, the solids are removed by filtration and the solvents are removed by evaporation under vacuum. The crude reaction product is chromatographed on coarse silica gel eluting with methylene chloride changing to 10% and 20% ethyl acetate/methylene chloride to yield (3S,4R)-3-[1-(2,2,2)-trichloroethoxycarbonyloxyethyl)-4-(triphenylmethylthio)azetidin-2-one].

(b) Add to a 500 ml flask 25 gm ketomalonic acid 1.5 H$_2$O, 250 mg p-toluene sulfonic acid, 58 gm allyl alcohol and 200 ml benzene. Reflux with a Dean Stark tube for 6.5 hours. Remove excess allyl alcohol and benzene by evaporation under vacuum. Wash the residue with H$_2$O, then distill at 2 mmHg and collect diallyl ketomalonate as a yellow oil. Add 25 gms of diallyl ketomalonate to 14.9 gm of trimethylsilylethanol, then add ½ ml of 1,5-diazabicyclo[4.3.0]non-5-ene(DBN). After 24 hours, wash the resultant mixture with cold 10% phosphoric, then with water. Dry the resultant product and distill at 0.4 mmHg to obtain allyl trimethylsilylethylketomalonate.

(c) Add 100 mg of (3S,4R)-3-[1-(2,2,2)-trichloroethoxycarbonyloxyethyl]-4-(triphenylmethylthio)-azetidin-2-one and 0.2 ml of dimethylformamide to a dry vial. Add 45 mg of allyl trimethylsilylethylketomalonate, 0.0014 ml of pyridine and 0.0014 ml of triethylamine to the system. Let stand at room temperature for 50 minutes, then remove the solvent to give (3S,4R)-1-[1-hydroxy-1-allyloxycarbonyl-1-trimethylsilylethoxycarbonylmethyl]-3-[1-(2,2,2)-trichloroethoxycarbonyloxyethyl)]-4-triphenylmethylthio)azetidin-2-one.

(d) Add 4.26 gm of (3S,4R)-1-[1-hydroxy-1-alloxycarbonyl-1-trimethylsilylethoxycarbonylmethyl]-3-[1-(2,2,2-trichloroethoxycarbonyloxyethyl)]-4-triphenylmethylthio)azetidin-2-one to a solution of 10 ml of methylene chloride, 2 ml pyridine and 1 gm of calcium carbonate. Cool the system to 0°-5° C. by placing the system in an ice bath. After cooling, slowly add 1.5 ml of thionyl chloride. After 25 minutes, the reaction is complete. Wash the reaction mixture with sodium bicarbonate solution of pH less than 8 and remove the solvent by stripping. Chromatograph the residue on silica gel using methlene chloride as the eluant to obtain (3S,4R)-1-[1-allyloxycarbonyl-1-chloro-1-trimethylsilylethoxycarbonylmethyl]-3-[1-(2,2,2)-trichloroethoxycarbonyloxyethyl]-4-(triphenylmethylthio)-azetidin-2-one.

(e) Dissolve 3.48 gm of (3S,4R)-1-[1-allyloxycarbonyl-1-chloro-1-trimethylsilylethoxycarbonylmethyl]-3-[1-(2,2,2)-trichloroethoxycarbonyloxyethyl]-4-(triphenylmethylthio)azetidin-2-one in 50 ml of tetrahydrofuran. To the system add 15 ml of water and 8 gm of zinc dust. Place the system in an ice bath and add 16 gm of ammonium chloride in portions over 1 hour. Stir the solution at 0°-5° C. for an additional 2 hours and then add 4 ml of gl. acetic acid and, portionwise, an additional 6 gms of zinc dust. Continue the reaction for an additional 1 hour, filter and remove the solvent by stripping. Dissolve the crude product in methylene chloride and wash the orgnic solution with water. Purify the crude product by column chromatography on silica gel using as eluant 1% ethylacetate (methylene chloride changihg to 25% ethylacetate) to obtain (3S,4R)-1-(1-allyloxycarbonyl-1-trimethylsilylethoxycarbonylmethyl]-3-(1-hydroxyethyl)4-(triphenylmethylthio)azetidin-2-one.

(f) To a 50 ml flask equipped with a nitrogen atmosphere add 5 ml of methanol and 1 gm (0.00158 moles) of (3S,4R)-1-[1-alloxycarbonyl-1-trimethylsilylethoxycarbonylmethyl]-3-(1-hydroxyethyl)-4-triphenylmethylthioazetidin-2-one. Cool the solution to about 0° C. and then add 0.14 ml of pyridine and 1.74 ml of methanol containing 294 mg (0.00173 moles) of silver nitrate. Stir the system at about 0° C. for 1 hour and then allow the system to warm to room temperature. After 2 hours of stirring at room temperature, add an additional 0.2 ml of methanol containing 34 mg of silver nitrate (0.0002 moles) to the system and continue the reaction for an additional 1 hour. Stop the reaction and remove the methanol by stripping. Dissolve the residue in methylene chloride and wash the organic solution twice with water, then with brine. Dry the organic solution over anhydrous sodium sulfate, filter and remove the methylene chloride by stripping to give silver (3S,4R)-3-(1-hydroxyethyl)-1-allyloxycarbonyl-1-trimethylsilylethoxycarbonylmethyl-azetidin-2-one-4-thiolate.

(g) Dissolve the entire amount of silver (3S,4R)-3-(1-hydroxyethyl)-1-allyloxycarbonyl-1-trimethylsilylethoxycarbonylmethylazetidin-2-one-4-thiolate obtained from step (f) above in 10 ml of anhydrous methylene chloride. Add 0.783 ml (0.00316 moles) of bis trimethylsilyl acetamide to the system. Stir the system at room temperature for 15 minutes to yield silver (3S,4R)-3-(1-trimethylsilyloxyethyl)-1-allyloxycarbonyl-1-trimethylsilylethoxycarbonyl-methyl azetidin-2-one-4-thiolate.

(h) After the completion of step (g) and to the same solution, add 619 mg (0.00316 moles) of 90% thiocarbonyl diimidazole to the system. Stir the system at room temperature for 20 hours and then filter the solution. Remove the methylene chloride by stripping. Chromatograph the crude product on silica gel eluting with 30% cyclohexane/methylene chloride changing to methylene chloride to yield (5R,6S,8R)-2-thiocarbonyl-3-allyloxycarbonyl-3-trimethylsilylethoxycarbonyl-6-(1-trimethylsilyloxyethyl)penam.

(i) To a 25 ml flask add 100 mg of (5R,6S,8R)-2-thiocarbonyl-3-allyloxycarbonyl-3-trimethylsilylethoxycarbonyl-6-(1-trimethylsilyloxyethyl)penam, 1 ml of tetrahydrofuran 0.05 ml of water and 0.05 ml of acetic acid. Stir the system at room temperature for 12 hours. Add ethyl acetate to the solution and wash the organic phase with sodium bicarbonate solution, water and then brine. Dry the organic phase over anhydrous sodium sulfate, filter and remove the solvent by stripping to give (5R,6S,8R)-2-thiocarbonyl-3-allyloxycarbonyl-3-trimethylsilylethoxycarbonyl-6-(1-hydroxyethyl)penam.

(j) To 7.7 mg of (5R,6S,8R)-2-thiocarbonyl-3-allyloxycarbonyl-3-trimethylsilylethoxy-carbonyl-6-(1-trimethylsilyloxyethyl)penam in 1 ml of tetrahydrofuran slowly add at room temperature 2 equivalents of tetrabutylammonium fluoride in 40 ml of tetrahydrofuran. Thin layer chromatography (silica gel, 10% ethylacetate/methylene chloride) shows the immediate presence of the monodeprotected decarboxylated compound (5R,6S,8R)allyl-2-thiol-6-(1-hydroxyethyl)-penem-3-carboxylate, which exists in equilibrium with (5R,6S,8R)-allyl-thiocarbonyl-6-(1-hydroxyethyl)penam-3-carboxylate.

(k) To a solution of (5R,6S,8R)-allyl-2-thio-6-(1-hydroxyethyl)penem-3-carboxylate and (5R,6S,8R)-allyl-2-thiocarbonyl-6-(1-hydroxyethyl)penam-3-carboxylate, add 2 ml of ethyl iodide. Separate the organic layer after partitioning between water and ethyl acetate. Remove the solvents by rotary evaporation to obtain (5R,6S,8R)allyl-2-ethylthio-6-(1-hydroxyethyl)penem-3-carboxylate which is converted to (5R,6S,8R)sodium-2-ethylthio-6-(1-hydroxyethyl)penem-3-carboxylate as described in U.S. Pat. No. 4,314,942.

We claim:

1. A process for preparing a compound represented by the formula

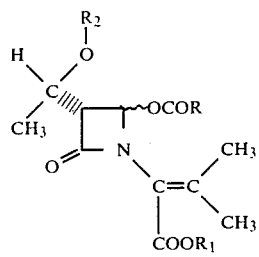

I wherein
R is lower alkyl, phenyl or phenyl substituted with up to three substitutents independently selected from nitro, halo or lower alkyl;
$R_1$ is lower alkyl, allyl, or a metabolizable ester group;
$R_2$ is a readily removable hydroxy protecting group; and
the wavy line means either the R stereochemical configuration, the S stereochemical configuration or a mixture thereof,
which comprises treating a compound represented by the formula

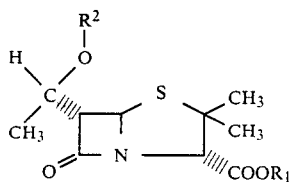

wherein $R_1$ and $R_2$ are as defined for formula II with a compound represented by the formula

wherein R is as defined for formula I in an inert organic solvent at temperatures between about 5° and 20 °C., followed by treatment with triethyl amine and recovery of the compound of formula I.

2. The process of claim 1 wherein the compound of formula II is (5R,6S,8R)methyl-6-(1-trichloroethoxycarbonylethyl)penicillinate and the compound of formula III is acetyl nitrate.

* * * * *